United States Patent [19]

Branca et al.

[11] 4,361,511
[45] Nov. 30, 1982

[54] BENZODIAZEPINE DERIVATIVES

[75] Inventors: Quirico Branca, Birsfelden; Albert E. Fischli, Riehen, both of Switzerland; Andre' Szente, Dee Why, Australia

[73] Assignee: Hoffmann-La Roche Inc., Nutley, N.Y.

[21] Appl. No.: 225,746

[22] Filed: Jan. 16, 1981

[30] Foreign Application Priority Data

Feb. 8, 1980 [CH] Switzerland .................. 1039/80

[51] Int. Cl.³ .......................................... C07D 243/24
[52] U.S. Cl. .......................... 260/239.3 D; 424/244; 424/246; 424/248.54; 424/270; 424/274; 424/250
[58] Field of Search .................. 260/239.3 D

[56]  References Cited
U.S. PATENT DOCUMENTS 3,371,085 2/1968 Reeder et al. ............... 260/239.3 D
3,464,978 9/1969 Earley et al. ................ 260/239.3 D
4,251,444 2/1981 Fischli et al. ............... 260/239.3 D Primary Examiner—Robert T. Bond
Attorney, Agent, or Firm—Jon S. Saxe; Bernard S. Leon; Frank P. Hoffmann

[57] ABSTRACT

There are presented compounds of the formula

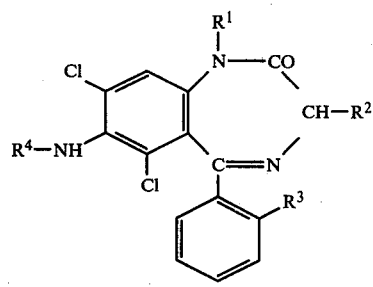

wherein $R^1$ is a lower alkyl group, $R^2$ is a hydrogen atom or a lower alkyl group, $R^3$ is a hydrogen or halogen atom, $R^4$ is a hydrogen atom or a group of the formula $R^5-CO-$, $R^6R^7N-O-$,

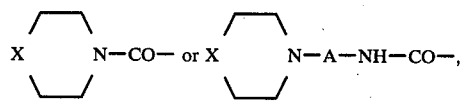

A is a lower alkylene group, X is an oxygen or sulphur atom or a group of the formula $>N-^8$, $R^5$ is a lower alkyl or lower haloalkyl group, $R^6$ is a hydrogen atom or a lower alkyl group, $R^7$ is a lower alkyl group and $R^8$ is a hydrogen atom or a lower alkyl or lower hydroxyalkyl group, and their pharmaceutically acceptable acid addition salts.

The compounds have aldosterone-antagonistic properties and are accordingly suitable for the control or prevention of heart failure, hepatic ascites, primary aldosteronism and idiopathic hypertension.

12 Claims, No Drawings

BENZODIAZEPINE DERIVATIVES

DESCRIPTION OF THE INVENTION

The benzodiazepine derivatives provided by the present invention are componds of the formula

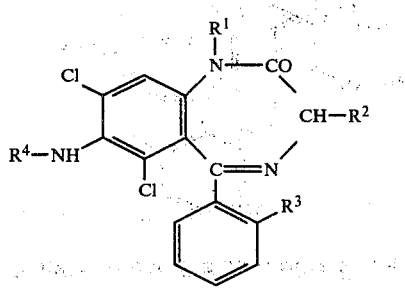

wherein $R^1$ is a lower alkyl group, $R^2$ is a hydrogen atom or a lower alkyl group, $R^3$ is a hydrogen or halogen atom, $R^4$ is a hydrogen atom or a group of the formula $R^5$—CO—, $R^6R^7N$—CO—,

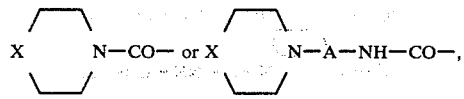

A is a lower alkylene group, X is an oxygen or sulphur atom or a group of the formula >N-$R^8$, $R^5$ is a lower alkyl or lower haloalkyl group, $R^6$ is a hydrogen atom or a lower alkyl group, $R^7$ is a lower alkyl group and $R^8$ is a hydrogen atom or a lower alkyl or lower hydroxyalkyl group, and pharmaceutically acceptable acid addition salts thereof.

The foregoing compounds and salts are novel and possess valuable pharmacodynamic properties.

Objects of the present invention are compounds of formula I and pharmaceutically acceptable acid addition salts thereof per se and as pharmaceutically active substances, the manufacture of said compounds and salts and intermediates for the manufacture of said compounds, medicaments containing a compound of formula I or a pharmaceutically acceptable acid addition salt thereof, the manufacture of such medicaments, as well as the use of compounds of formula I or of pharmaceutically acceptable acid addition salts thereof in the control or prevention of illnesses.

As used in this Specification, the term "lower alkyl", alone or in combinations such as in "lower hydroxyalkyl", "lower haloalkyl" and the like, denotes straight-chain or branched-chain saturated hydrocarbon groups containing at most 7, preferably at most 4, carbon atoms such as methyl, ethyl, n-propyl, isopropyl, n-butyl, tert-.butyl etc. The term "lower hydroxyalkyl" includes groups such as 2-hydroxyethyl, 3-hydroxy-2-propyl and the like. The term "lower haloalkyl" includes hydrocarbon groups carrying one or more halogen atoms such as trifluoromethyl, 2-chloroethyl, 3,3-dichloro-2-propyl and the like. The term "halo" means fluoro, chloro, bromo or iodo and the term "halogen" means fluorine, chlorine, bromine or iodine. The term "lower alkylene" denotes divalent saturated hydrocarbon groups which contain at most 7, preferably at most 4, carbon atoms and which can be straight-chain or branched-chain such as methylene, ethylene, 1,2-propylene, ethylidene and the like.

Preferred among the compounds of formula I are those in which $R^1$ represents a methyl group. $R^2$ in formula I preferably represents a hydrogen atom or a methyl group. $R^3$ in formula I preferably represents a hydrogen, fluorine or chlorine atom. $R^4$ in formula I preferably represent a hydrogen atom or a group of the formula

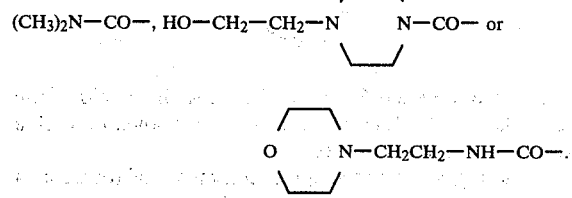

Quite especially preferred compounds of formula I are:

3-[6,8-Dichloro-5-(o-fluorophenyl)-2,3-dihydro-1-methyl-2-oxo-1H-1,4-benzodiazepin-7-yl]-1,1-dimethylurea, N-[6,8-dichloro-5-(o-fluorophenyl)-2,3-dihydro-1-methyl-2-oxo-1H-1,4-benzodiazepin-7-yl]-4-(2-hydroxyethyl)-1-piperazinecarboxamide and 1-[6,8-dichloro-5-(o-fluorophenyl)-2,3-dihydro-1-methyl-2-oxo-1H-1,4-benzodiazepin-7-yl]-3-(2-morpholinoethyl)urea.

Other compounds of formula I which are preferred are:

7-Amino-6,8-dichloro-5-phenyl-1,3-dihydro-1-methyl-2H-1,4-benzodiazepin-2-one, 7-amino-6,8-dichloro-5-(o-chlorophenyl)-1,3-dihydro-1,3-dimethyl-2H-1,4-benzodiazepin-2-one, 3-[6,8-dichloro-5-(o-fluorophenyl)-2,3-dihydro-1-methyl-2-oxo-1H-1,4-benzodiazepin-7-yl]-1-methylurea, N-[6,8-dichloro-5-(o-fluorophenyl)-2,3-dihydro-1-methyl-2-oxo-1H-1,4-benzodiazepin-7-yl]-2,2,2-trifluoroacetamide and 7-amino-6,8-dichloro-5-(o-fluorophenyl)-1,3-dihydro-1-methyl-2H-1,4-benzodiazepin-2-one.

According to the process provided by the present invention, the benzodiazepine derivatives aforesaid (i.e. the compounds of formula I and their pharmaceutically acceptable acid addition salts) are manufactured by (a) chlorinating a benzodiazepine derivatives of the formula

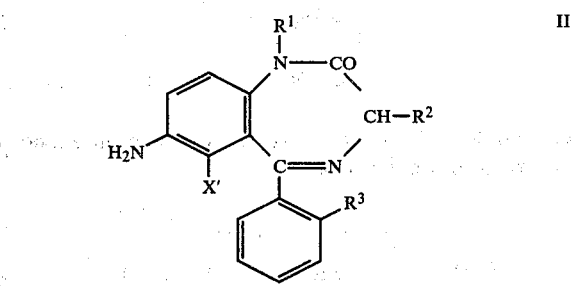

wherein $R^1$, $R^2$ and $R^3$ are as above and X' is a hydrogen or chlorine atom, or (b) acylating a benzodiazepine derivative of the formula

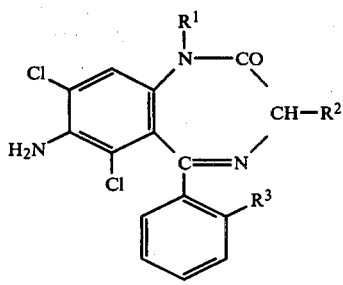
Ia wherein $R^1$, $R^2$ and $R^3$ are as above, with an acid of the formula $R^5$—COOH, wherein $R^5$ is as above, or with a reactive derivative thereof, or (c) reacting a benzodiazepine derivative of formula Ia hereinbefore with a halide of the formula

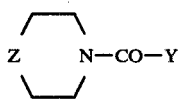
III
IV wherein Y is a halogen atom, $R^{61}$ and $R^{71}$ each are a lower alkyl group, Z is an oxygen or sulphur atom or a group of the formula $>$N-$R^{81}$ and $R^{81}$ is a lower alkyl group, (d) reacting a benzodiazepine derivative of formula Ia hereinbefore with an isocyanate of the formula

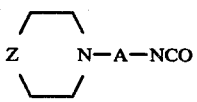
V
VI wherein A, Z and $R^{71}$ are as above, or (e) reacting a benzodiazepine derivative of the formula

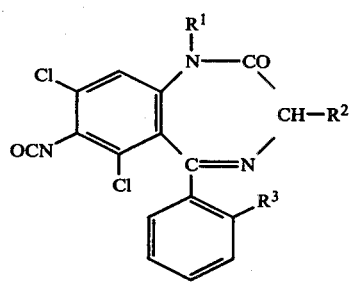
VII wherein $R^1$, $R^2$ and $R^3$ are as above, with an amino compound of the formula

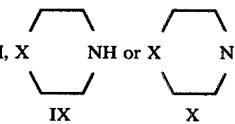 
VIII IX X wherein A, X, $R^6$ and $R^7$ are as above, or (f) removing the protecting group(s) from a benzodiazepine derivative of the formula

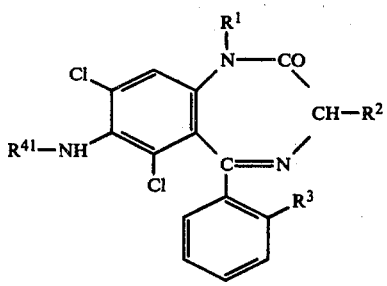
XI wherein $R^{41}$ is a protecting group or a group of the formula

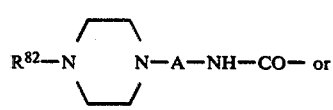

U is an oxygen or sulphur atom or a group of the formula $>$N-$R^{83}$, $R^{62}$ is a protecting group, $R^{72}$ is a lower alkyl group, $R^{82}$ is a protecting group or a group of the formula —A—O—V, $R^{83}$ is a hydrogen atom, a lower alkyl group, a lower hydroxyalkyl group, a protecting group or a group of the formula —A—O—V and $R^9$ and V each are a protecting group and $R^1$, $R^2$, $R^3$ and A are as above, or (g) converting a benzodiazepine derivative of the formula

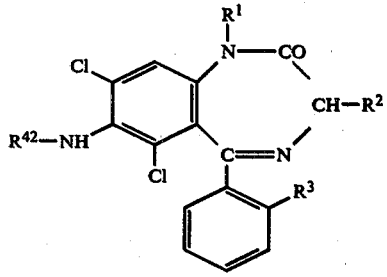
XII wherein $R^{42}$ is a group of the formula

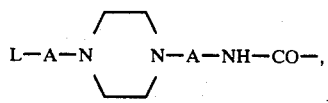

L is a leaving group and $R^1$, $R^2$, $R^3$ and A are as above, into a corresponding hydroxy compound, or (h) reacting a benzodiazepine derivative of the formula

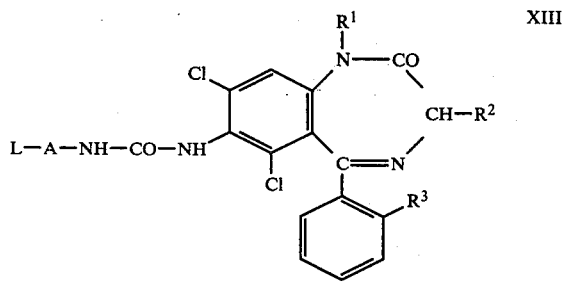

wherein $R^1$, $R^2$, $R^3$, A and L are as above, with an amino compound of formula IX hereinbefore, or (i) alkylating a benzodiazepine derivative of the formula

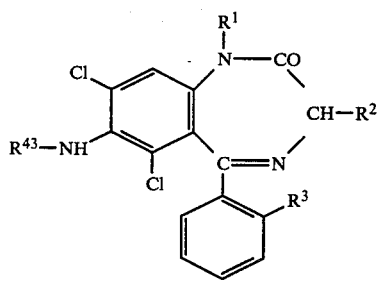

wherein $R^{43}$ is a group of the formula

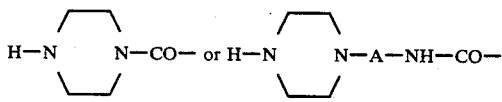

and $R^1$, $R^2$, $R^3$ and A are as above, or (k) cyclising a benzophenone derivative of the formula

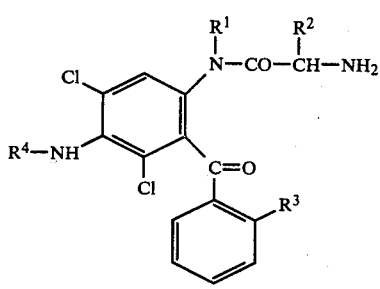

wherein $R^1$, $R^2$, $R^3$ and $R^4$ are as above, or (l) converting a compound of formula I into a pharmaceutically acceptable acid addition salt.

According to embodiment (a) of the process, compounds of formula I can be manufactured by chlorinating a benzodiazepine derivative of formula II. The chlorinating agent is conveniently a compound such as N-chlorosuccinimide, N-chloroacetamide or the like. The solvent is preferably a halogenated hydrocarbon such as methylene chloride, dichloroethane, chloroform, etc, although other organic solvents which are inert under the conditions of the chlorination (e.g. acetonitrile, ether etc) can also be used. The chlorination is conveniently carried out at a temperature of about 0° C. to room temperature.

Elemental chlorine can also be used as the chlorinating agent, this chlorination conveniently being carried out in acidic-aqueous solution with hydrogen chloride being the preferred acid. This chlorination is conveniently carried out at about $-10°$ C. to $+10°$ C., preferably at 0° C.

According to embodiment (b) of the process, compounds of formula I can be manufactured by acylating a benzodiazepine derivative of formula Ia with an agent yielding the residue $R^5$—CO—. This acylation can be carried out with any suitable acylating agent, for example with an acid anhydride such as trifluoroacetic acid anhydride, with an acid halide such as acetyl chloride etc. The acylation conditions can readily be chosen by a person skilled in the art depending on the acylating agent used. For example, the acylation can be carried out at room temperature or at a temperature above or below room temperature. The acylation is conveniently carried out in an organic solvent which is inert under the conditions of the acylation, for example, acetonitrile or the like, methylene chloride, dichloroethane or the like, tetrahydrofuran, dimethoxyethane or the like etc, and in the presence of an acid-binding agent, for example an inorganic base such as potassium carbonate, sodium carbonate etc or a tertiary organic amino compound such as triethylamine, N-ethyl-diisopropylamine, quinuclidine etc.

According to embodiment (c) of the process, compounds of formula I can be manufactured by reacting a benzodiazepine derivative of formula Ia with a halide of formula III or IV. This reaction is carried out in the presence of an acid-binding agent; for example, an inorganic base such as potassium carbonate, sodium carbonate etc or an organic base such as a tertiary amino compound (e.g. triethylamine, N-ethyl-diisopropylamine, quinuclidine etc). The reaction is conveniently carried out at room temperature or at a temperature below room temperature. The reaction proceeds fairly slowly and generally takes several days.

According to embodiment (d) of the process, compounds of formula I can be manufactured by reacting a benzodiazepine derivative of formula Ia with an isocyanate of formula V or VI. This reaction is conveniently carried out in an organic solvent which is inert under the reaction conditions; for example, a halogenated hydrocarbon such as methylene chloride, dichloroethane, chloroform, o-dichlorobenzene etc) an ether such as tetrahydrofuran, dioxan, dimethoxyethane, diethyleneglycol dimethyl ether etc or the like. In many cases it has been found to be favourable to carry out the reaction in the presence of a catalytically-acting small amount of a base; for example, a tertiary amino compound such as triethylamine, N-ethyldiisopropylamine, quinuclidine etc. The temperature at which this reaction is carried out is not critical and the reaction can be carried out at room temperature, at a temperature below room temperature or at a temperature above room temperature (e.g. at the reflux temperature).

According to embodiment (e) of the process, the compounds of formula I can be manufactured from benzodiazepine derivatives of formula VII and amino compounds of formula VIII, IX or X. In this case, the benzodiazepine derivative of formula VII is conveniently prepared in the manner described hereinafter from the corresponding benzodiazepine derivative of formula Ia shortly or immediately before the reaction with the amino compound of formula VIII, IX or X and is introduced into the reaction not in isolated form but in the solution in which it has previously been prepared from the corresponding benzodiazepine derivative of formula Ia.

An amino compound of formula VIII, IX or X can then be added to the aforementioned solution containing the benzodiazepine derivative of formula VII. In so doing, the amino compound of formula VIII, IX or X can be used in the form of a solution or in the absence of a solvent. Where an amino compound which is gaseous at room temperature is used (e.g. in the case of methylamine), it can be introduced as the gas into the aforementioned solution containing the benzodiazepine derivative of formula VII.

On the other hand, it is also possible to add the aforementioned solution containing the benzodiazepine derivative of formula VII to the amino compound of formula VIII, IX or X, conveniently in the form of a solution.

In many cases it is convenient to use an excess of amino compound of formula VIII, IX or X and this is indeed necessary when it contains more than one nitrogen atom which is capable of reacting with an isocyanate group (e.g. in the case of piperazine).

Various organic solvents which are inert under the reaction conditions (e.g. halogenated hydrocarbons such as dichloroethane, methylene chloride, chloroform, o-dichlorobenzene etc, ethers such as tetrahydrofuran, dioxan, dimethoxyethane, diethyleneglycol dimethyl ether etc or the like) are suitable for embodiment (e) of the process.

The reaction of a benzodiazepine derivative of formula VII with an amino compound of formula VIII, IX or X is conveniently carried out at room temperature or at a temperature below room temperature.

When the amino compound of formula VIII, IX or X is added to a solution of the benzodiazepine derivative of formula VII, the addition should be carried out within a short time, whereas in the opposite case (i.e. when the solution of the benzodiazepine derivative of formula VII is added to the amino compound of formula VIII, IX or X), the promptness with which the addition is carried out is not critical.

According to embodiment (f) of the process, compounds of formula I can be manufactured by removing the protecting group or the protecting groups from a benzodiazepine derivative of formula XI. Suitable nitrogen-protecting groups for the purpose of the present invention are primarily acyl groups, preferably readily cleavable alkoxycarbonyl or aralkoxycarbonyl groups, especially tert.butoxycarbonyl, benzolyxycarbonyl etc. as well as readily cleavable aralkyl groups such as benzyl. Suitable oxygen-protecting groups are on the one hand acyl groups or aralkyl groups such as those mentioned earlier as nitrogen-protecting groups and on the other hand ketal protecting groups such as tetrahydropyranyl, 2-methoxy-2-propyl, methoxymethyl, β-methoxyethoxy-methyl etc, readily cleavable alkyl groups such as tert.butyl etc. or alkanoyl groups such as acetyl and the like.

The removal of the protecting group or of the protecting groups from the benzodiazpine derivatives of formula XI is carried out according to methods known per se, whereby, of course, the nature of the protecting group or protecting group to be removed must be taken into consideration when choosing the method or methods used for the removal. In addition, it will, of course, be appreciated that only those methods can be used which selectively remove the protecting group or protecting groups without affecting other structural elements present in the molecule.

The groups mentioned earlier as examples of protecting groups can be cleaved off, depending on their nature, hydrogenolytically and/or hydrolytically. Thus, for example, the benzyloxycarbonyl group and the tert.butoxycarbonyl group can be cleaved off under selective acidic conditions; for example, by treatment with a mixture of hydrogen bromide and glacial acetic acid or by treatment with boron trifluoride or boron tribromide in an inert organic solvent such as dichloromethane. The tert.butoxycarbonyl group can also be cleaved off by treatment with hydrogen chloride in an inert solvent such as dioxan, tetrahydrofuran or the like or by treatment with trifluoroacetic acid. The tetrahydropyranyl group can be cleaved off under mild acidic conditions; for example, by treatment with dilute aqueous mineral acid under mild conditions. The tert.butyl group can be cleaved off, for example using trifluoroacetic acid. The benzyl group can be cleaved off by catalytic hydrogenation (e.g. over palladium/carbon). The acetyl group can be cleaved off under mild alkaline conditions; for example, with a solution of a sodium alcoholate in the corresponding alcohol (e.g. methanolic sodium methylate).

According to embodiment (g) of the process, compounds of formula I can be manufactured by converting a benzodiazepine derivative of formula XII into a corresponding hydroxy compound. The leaving group denoted by L in formula XII can be a halogen atom, especially a chlorine, bromine or iodine atom, or can be an equivalent leaving group (e.g. an arylsulphonyloxy group such as tosyloxy, an alkylsulphonyloxy group such as mesyloxy, a quaternary ammonium group such as the trimethylammonium group etc).

The conversion of a benzodiazepine derivative of formula XII into a corresponding hydroxy compound can be carried out, for example, by solvolysis in a water-containing system, conveniently in a mixture of an aromatic hydrocarbon (e.g. benzene) and water in the presence of a quaternary ammonium salt such as tetrabutylammonium bromide and at a temperature between room temperature and the reflux temperature of the mixture.

According to embodiment (h) of the process, compounds of formula I can be manufactured by reacting a benzodiazepine derivative of formula XIII with an amino compound of formula IX hereinbefore. The leaving group denoted by L in formula XIII can be a halogen atom, especially a chlorine, bromine or iodine atom, or can be an equivalent leaving group (e.g. an arylsulphonyloxy group such as tosyloxy, an alkylsulphonyloxy group such as mesyloxy etc.)

The reaction of a benzodiazepine derivative of formula XIII with an amino compound of formula IX is conveniently carried out in an organic solvent which is inert under the reaction conditions, for example an ether such as diethyl ether, tetrahydrofuran, dioxan etc, an alcohol, such as ethanol, ethyleneglycol etc or the like, in the presence of an acid-binding agent, for example an inorganic base such as potassium carbonate, sodium carbonate etc. or an organic base such s triethylamine, excess amino compound of formula IX etc. An excess of amine of formula IX is required when it contains two reactive amino groups (e.g. in the case of piperazine). The reaction temperature can be varied within a wide range from 0° C. to the boiling point of the reaction mixture depending on the reactivity of the leaving group denoted by L.

According to embodiment (i) of the process, the compounds of formula I can be manufactured by alkylating a benzodiazepine derivative of formula Ib; the term "alkylating" being used in this context to mean the introduction of a lower alkyl group or a lower hydroxyalkyl group. This reaction can be carried out using any suitable alkylating agent, for example a corresponding halide such as methyl iodide, 2-bromoethanol, iodoethane etc. or a dialkyl sulphate such as dimethyl sulphate or diethyl sulphate in the presence of an acid-binding agent, using an aldehyde such as formaldehyde, acetaldehyde etc under reducing conditions, using a corresponding epoxy compound such as ethylene oxide and the like.

The conditions under which the alkylation is carried out can be chosen by a person skilled in the art depending on the alkylating agent used. For example, the benzodiazepine derivative of formula Ib can be boiled at reflux with an equivalent amount of an appropriate aldehyde in formic acid until carbon dioxide no longer evolves, the solvent can then be removed in vacuo and the free base can be isolated by neutralisation.

According to embodiment (k) of the process, the compounds of formula I can be manufactured by cyclising a benzophenone derivative of formula XIV. The cyclisation is carried out fairly readily; it can be brought about by standing for a long time or can be expedited by the use of heat. The cyclisation can be carried out in neutral, alkaline or acidic medium, preferably in an alkaline medium. The cyclisation is conveniently carried out in an inert organic solvent; for example, a hydrocarbon such as benzene, toluene etc, a chlorinated hydrocarbon such as chloroform, methylene chloride etc, an ether such as dioxan etc. Suitable temperatures for the cyclisation of the benzophenone derivatives of formula XIV are temperatures between room temperature and about 150° C. depending, of course, on the solvent used.

The benzophenone derivatives of formula XIV need not necessarily be used in isolated form and in many cases this is not possible. Generally, it has been found to be convenient to cyclise the benzophenone derivatives of formula XIV directly or to leave them to cyclise without isolation from the mixture in which they have been prepared.

According to embodiment (l) of the process, the compounds of formula I can be converted into pharmaceutically acceptable acid addition salts. The manufacture of such pharmaceutically acceptable acid addition salts is carried out according to generally customary methods. There come into consideration not only salts with inorganic acids but also salts with organic acids; for example, hydrochlorides, hydrobromides, sulphates, citrates, acetates, succinates, methanesulphonates, p-toluenesulphonates and the like.

The benzodiazepine derivatives of formula II used as starting materials in embodiment (a) of the process belong to a class of compound known per se and many specific representatives of this class of compound have already been described in the literature. Representatives which have not previously been specifically described can be prepared according to methods which are known per se and familiar to a person skilled in the art. Conveniently, benzodiazepine derivatives of formula II are prepared from corresponding nitro compounds of the formula

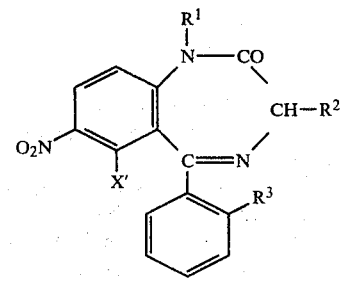

wherein $R^1$, $R^2$, $R^3$ and $X'$ are as above. These nitro compounds likewise belong to a class of compound known per se of which various specific representatives are described in the literature. Representatives which have not previously been specifically described can be prepared according to methods which are familiar to a person skilled in the art and which can be carried out in analogy to those methods which are described for the preparation of the specifically previously known compounds.

The conversion of a nitro compound of formula XV into a corresponding benzodiazepine derivative of formula II is carried out by reduction of the nitro group, conveniently using stannous chloride, zinc, catalytically activated hydrogen, etc. When $X'$ in formula XV represents a hydrogen atom and a benzodiazepine derivative of formula II in which $X'$ represents a chlorine atom is desired, a chlorination must be carried out subsequent to the aforementioned reduction. This chlorination is conveniently carried out using elemental chlorine in acidic-aqueous solution, hydrogen chloride conveniently being used as the acid.

The benzodiazepine derivatives of formula VII used as starting materials in embodiment (e) of the process can be prepared, as mentioned earlier, from corresponding benzodiazepine derivatives of general formula Ia, namely by reaction with phosgene. In this case, a solution of phosgene in an organic solvent which is inert under the reaction conditions is conveniently treated with a solution of a benzodiazepine derivative of formula Ia while cooling, the mixture is then heated to reflux for a period, again cooled down and finally the solution obtained is made basic or at least neutral with a tertiary organic amino compound such as triethylamine. The resulting solution, containing a benzodiazepine derivative of formula VII, can be stored for several hours with the exclusion of moisture and in the cold; it is, as mentioned earlier, used directly in the process without isolation of the benzodiazepine derivative of formula VII contained therein.

The benzodiazepine derivatives of formula VII are also an object of the present invention.

For the preparation of benzodiazepine derivatives of formula XI used as starting materials in embodiment (f) of the process, a compound of the formula

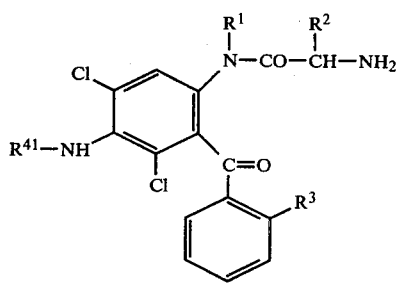 XVI wherein $R^1$, $R^2$, $R^3$ and $R^{41}$ are as above, can be cyclised (in analogy to the cyclisation of benzophenone derivatives of formula XIV; see earlier).

The benzodiazepine derivatives of formula XI are also an object of the present invention.

Benzodiazepine derivatives of formula XI can, however, also be prepared from benzodiazepine derivatives of formula VII or Ia according to methods known per se, whereby, of course, the nature of the protecting group or protecting groups whose presence is desired in the benzodiazepine derivative of formula XI to be prepared must be taken into consideration when choosing the method or methods used.

For the preparation of a benzodiazepine derivative of formula XI in which $R^{41}$ represents a group of the formula $R^{62}R^{72}N\text{-CO-}$ or

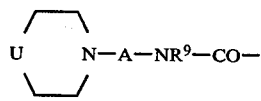

wherein U has the significance given earlier except that $R^{83}$ can only represent a lower alkyl group, a protecting group or a group of the formula -A-O-V, a benzodiazepine derivative of formula Ia can be reacted with a corresponding carbamoyl halide (in analogy to the method described earlier for the manufacture of compounds of formula I from benzodiazepine derivatives of formula Ia and halides of formula III).

For the preparation of benzodiazepine derivatives of formula XI in which $R^{41}$ represents a group of the formula

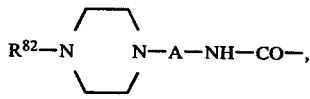

a benzodiazepine derivative of formula Ia can be reacted with a corresponding isocyanate (in analogy to the method described earlier for the manufacture of compounds of formula I from benzodiazepine derivatives of formula Ia and isocyanates of formula VI). A further possibility consists in reacting a benzodiazepine derivative of formula VII with a corresponding amine (in analogy to the method described earlier for the manufacture of compounds of formula I from benzodiazepine derivatives of formula VII and amino compounds of formula X). In this case, however, it will be appreciated that the protecting group (V,$R^{82}$) can not be an acyl group.

For the preparation of benzodiazepine derivatives of formula XI in which $R^{41}$ represents a group of the formula

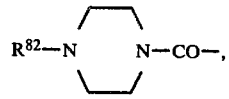

a benzodiazepine of formula Ia can be reacted with a corresponding carbamoyl halide (in analogy to the method described earlier for the manufacture of compounds of formula I from benzodiazepine derivatives of formula Ia and halides of formula III). A further possibility consists in reacting a benzodiazepine derivative of formula VII with a corresponding amine (in analogy to the method described earlier for the manufacture of compounds of formula I from benzodiazepine derivatives of formula VII and amino compounds of formula IX. Again, in this case, the protecting group (V,$R^{82}$) can not be an acyl group.

Benzodiazepine derivatives of formula XII used as starting materials in embodiment (g) of the process can be prepared from benzodiazepine derivatives of formula Ia according to methods known per se, namely by reaction with a corresponding carbamoyl chloride (in analogy to the method described earlier for the manufacture of compounds of formula I from benzodiazepine derivatives of formula Ia and halides of formula IV) or by reaction with a corresponding isocyanate (in analogy to the method described earlier for the manufacture of compounds of formula I from benzodiazepine derivatives of formula Ia and isocyanates of formula VI).

Benzodiazepine derivatives of formula XIII used as starting materials in embodiment (h) of the process can be prepared from benzodiazepine derivatives of formula Ia according to methods known per se, namely by reaction with a corresponding isocyanate (in analogy to the method described earlier for the manufacture of compounds of formula I from benzodiazepine derivatives of formula Ia and isocyanates of formula V).

The benzodiazepine derivatives of formulae XII and XIII are also objects of the present invention.

Benzodiazepine derivatives of formula XIV used as starting materials in embodiment (k) of the process can be prepared according to methods known per se; the preparative procedure being carried out, in part, in analogy to methods which are described earlier in connection with certain processes for the manufacture of compounds of formulae I and XI. As starting materials for the preparation of benzophenone derivatives of formula XIV there are conveniently used benzophenone derivatives of the formula

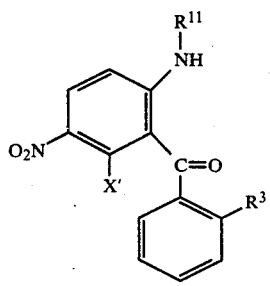

XVII wherein $R^3$ and $X'$ are as above and $R^{11}$ is a hydrogen atom or a lower alkyl group.

For example a benzophenone derivative of formula XVII can initially be converted into a compound of the formula

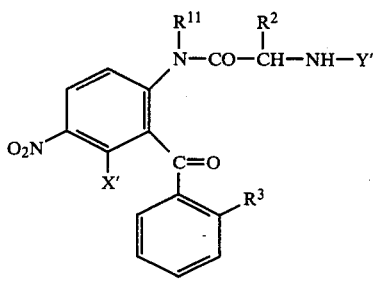

XVIII wherein $R^{11}$, $R^2$, $R^3$ and $X'$ are as above and $Y'$ is a protecting group, whereupon, where $R^{11}$ in formulae XVII and XVIII represents a hydrogen atom, the nitrogen atom is alkylated, the nitro group is reduced to the amino group and the resulting amino compound is chlorinated. Suitable protecting groups denoted by $Y'$ in formula XVIII are primarily acyl groups, preferably readily cleavable alkoxycarbonyl or aralkoxycarbonyl groups, especially the benzyloxycarbonyl group. Accordingly, for the manufacture of the compounds of formula XVIII from the benzophenone derivatives of formula XVII there are conveniently used corresponding acylaminoalkanoyl halides such as carbobenzoxyglycine chloride, carbobenzoxyalanine chloride, carbobenzoxy-α-aminobutyric acid chloride etc. Where it is necessary to carry out a N-alkylation, then this is carried out according to methods known per se; for example, using methyl iodide or the like in the presence of a base such as potassium carbonate, and in a suitable solvent such as acetone which is inert under the alkylation conditions. The reduction of the nitro to the amino group is conveniently carried out using stannous chloride and the like. The chlorination is conveniently carried out in analogy to the manufacture of compounds of formula Ia from benzodiazepine derivatives of formula II.

The 5-aminobenzophenone derivatives of the formula

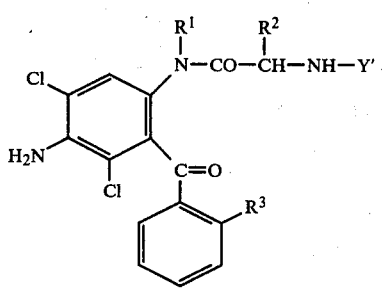

XIX wherein $R^1$, $R^2$, $R^3$ and $Y'$ are as above, obtained in the manner previously described are subsequently converted into corresponding compounds of the formula

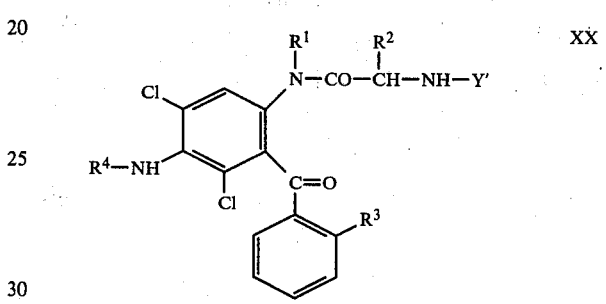

XX wherein $R^1$, $R^2$, $R^3$, $R^4$ and $Y'$ are as above. This conversion can be carried out, for example, by reacting a 5-aminobenzophenone derivative of formula XIX in analogy to methods described earlier with a halide of formula III or IV or an isocyanate of formula V or VI, or by converting a 5-aminobenzophenone derivative of formula XIX, in analogy to the method described earlier for the manufacture of the compounds of formula VII, into the corresponding isocyanate which is then reacted with an amino compound of formula VIII, IX or X in analogy to the method described earlier for the manufacture of compounds of formula I from benzodiazepine derivatives of formula V and amino compounds of formula VIII, IX or X, or by acylating a 5-aminobenzophenone derivative of formula XIX with an acid of the formula $R^5$-COOH, wherein $R^5$ has the significance given earlier, or with a reactive derivative thereof in analogy to the manufacture of compounds of formula I from benzodiazepine derivatives of formula Ia and an acid of the formula $R^5$-COOH or a reactive derivative thereof.

A corresponding benzophenone derivative of formula XIV is then obtained by cleavage of the protecting group denoted by $Y'$ from a compound of formula XX.

It is also possible to convert (in analogy to the method described earlier for the preparation of the benzodiazepine derivatives of general formula XII) a compound of formula XIX into a compound of the formula

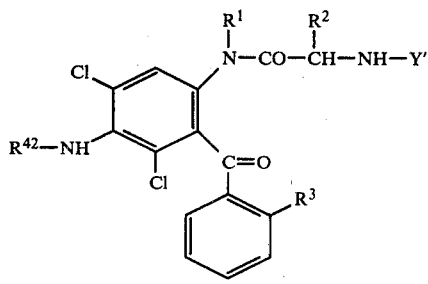

XXI wherein $R^1$, $R^2$, $R^3$, $R^{42}$ and $Y'$ are as above, thereupon to convert (in analogy to the method described earlier for the manufacture of compounds of formula I from benzodiazepine derivatives of formula XII) a compound of formula XXI into a corresponding hydroxy compound and thereupon to proceed to a corresponding compound of formula XIV by cleavage of the protecting group denoted by $Y'$. Furthermore, it is possible to convert a 5-aminobenzophenone derivative of formula XIX into a compound of the formula

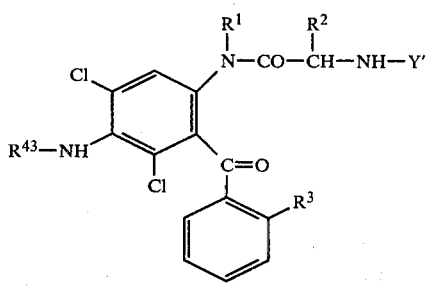

XXa wherein $R^1$, $R^2$, $R^3$, $R^{43}$ and $Y'$ are as above, whereupon a corresponding benzophenone derivative of formula XIV can be obtained by alkylation (in analogy to the method described earlier for the manufacture of compounds of formula I from benzodiazepine derivatives of formula Ib) and subsequent cleavage of the protecting group denoted by $Y'$.

Furthermore, it is possible to convert a 5-aminobenzophenone derivative of formula XIX into a compound of the formula

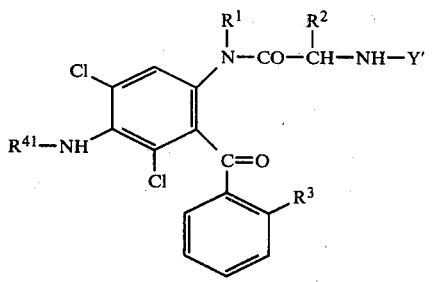

XXII wherein $R^1$, $R^2$, $R^3$, $R^{41}$ und $Y'$ are as above. This conversion can be carried out in analogy to the methods described earlier for the manufacture of the benzodiazepine derivatives of formula XI. Benzophenone derivatives of formula XIV are prepared from compounds of formula XXII by cleaving off the protecting group denoted by $Y'$ and, previously or in the same operation, the other protecting group or other protecting groups present in the molecule.

A further possibility for the preparation of benzophenone derivatives of formula XIV consists in converting a nitrobenzophenone derivative of formula XVII into a compound of the formula

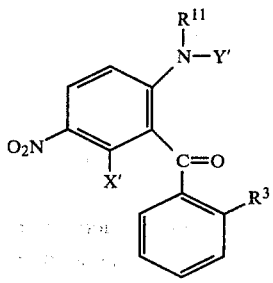

XXIII wherein $R^{11}$, $R^3$, $X'$ and $Y'$ are as above, thereupon, where $R^{11}$ in formula XXIII represents a hydrogen atom, alkylating the nitrogen atom, reducing the nitro group and chlorinating a 5-aminobenzophenone derivative obtained. The compounds obtained in this manner have the formula

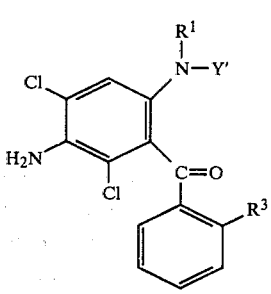

XXIV wherein $R^1$, $R^3$ and $Y'$ are as above,

A compound of the formula XXIV can then be converted into a compound of the formula

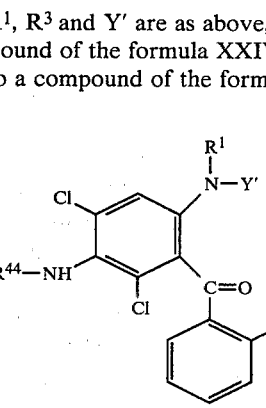

XXV wherein $R^{44}$ is a group of the formula $R^5$-CO-,

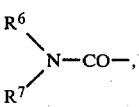

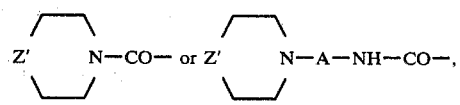

Z' is an oxygen or sulphur atom or a group of the formula >N-R$^{84}$, R$^{84}$ is a lower alkyl group and R$^1$, R$^3$, R$^5$, R$^6$, R$^7$, A and Y' are as above, for example, by reaction with a halide of formula III or IV or an isocyanate of formula V or VI (in analogy to the method described earlier for the manufacture of compounds of formula I from benzodiazepine derivatives of formula Ia), or with an acid of the formula R$^5$-COOH, wherein R$^5$ has the significance given earlier, or with a reactive derivative thereof (in analogy to the method described earlier for the manufacture of compounds of formula I from benzodiazepine derivatives of formula Ia and an acid of the formula R$^5$-COOH or a reactive derivative thereof), or by conversion into a corresponding isocyanate (in analogy to the method described earlier for the preparation of benzodiazepine derivatives of formula VII) and subsequent reaction of said isocyanate with an amino compound of formula VIII, IX or X (in analogy to the method described earlier for the manufacture of compounds of formula I from benzodiazepine derivatives of formula VII). By cleaving off the protecting group denoted by Y' from a compound of general formula XXV there is obtained a benzophenone derivative of the formula

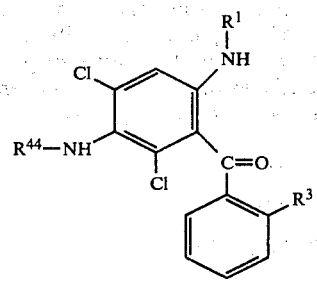

XXVI wherein R$^1$, R$^3$ and R$^{44}$ are as above.

Benzophenone derivatives of formula XXVI can be converted according to a large number of different methods known per se into corresponding benzophenone derivatives of formula XIV; for example, by reaction with a corresponding α-haloalkanoyl halide and treatment of the resulting compound with ammonia, by treatment with a corresponding α-aminoacylating agent carrying a suitable protecting group on the nitrogen atom (e.g. a corresponding α-benzyloxycarbonylaminoalkanoyl halide such as carbobenzoxyglycine chloride) and subsequent cleavage of the protecting group, by conversion into a corresponding α-azidoalkanoyl derivative (e.g. an azidoacetyl derivative) and subsequent reduction etc.

On the other hand, compounds of formula XXIV can also be converted (for example in analogy to the methods further described earlier for the preparation of benzodiazepine derivatives of formula XI) into corresponding compounds of the formula

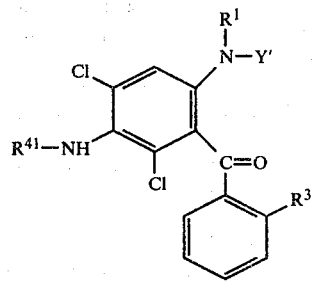

XXVII wherein R$^1$, R$^3$, R$^{41}$ and Y' are as above, whereupon the protecting group denoted by Y' is removed. It will be appreciated that the various protecting groups in a compound of formula XXVII must be provided so that the protecting group denoted by Y' can be removed without bringing about a cleavage of the other protecting group or protecting groups present in the molecule. A resulting compound is then converted according to methods known per se into a corresponding compound of formula XXII. This conversion can be carried out in analogy to the method described earlier for the preparation of the compounds of formula XXVIII from the compounds of formula XVII. The conversion of the compounds of formula XXII into corresponding benzophenone derivatives of formula XIV has been described earlier.

As mentioned earlier, it is not necessary (and in many cases also not possible) to isolate the benzophenone derivatives of formula XIV. On the contrary, it has generally been found to be convenient to cyclise these derivatives directly or to leave these derivatives to cyclise without isolation from the mixture in which they have been prepared.

The benzophenone derivatives of formula XIV are also an object of the present invention.

Compounds of formula XVI hereinbefore can be obtained by removing the protecting group denoted by Y' from a compound of formula XXII. It will be appreciated that the various protecting groups in a compound of formula XVI must be provided so that the protecting group denoted by Y' can be removed without bringing about a cleavage of the other protecting group or protecting groups present in the molecule.

Surprisingly, it has been shown that the compounds of formula I hereinbefore display no activity or only very slight activity on the central nervous system, whereas they exhibit pronounced aldosterone-antagonistic properties. These aldosterone-antagonistic properties can be demonstrated in adrenalectomised rats as illustrated hereinafter.

If aldosterone is administered to adrenalectomised rats, then there is observed, in comparison to untreated animals, a pronounced reduction of the sodium excretion (sodium retention), an increased potassium excretion (potassium excretion) as well as a reduction of the excreted urine volume. If compounds of formula I are administered to the animals before the treatment with aldosterone, then there is observed, in comparison to animals treated only with aldosterone (control animals), a pronounced increase of the sodium excretion (i.e. the sodium retention caused by aldosterone is antagonised), whereas the potassium excretion and the urine volume are influenced to a lesser extent.

The standard experiment is carried out as follows:

Female Holtzmann rats (150–180 g) are bilaterally adrenalectomised 70 to 74 hours before the beginning of the experiment. After the operation, the animals receive a customary rat dry feed and 0.9 percent sodium chloride solution for drinking. 16 to 17 hours before the beginning of the experiment the feed is removed from the animals, but they can subsequently drink, as before, 0.9 percent sodium chloride solution ad libitum. At the beginning of the experiment the substance to be tested as an aldosterone-antagonist is administered to the animals by means of a stomach probe. 30 minutes later the animals receive a subcutaneous injection of 4 mmg/kg of aldosterone. After a further 90 minutes, the urinary bladders of the animals are emptied by careful suprapubic pressure, whereupon the animals are placed individually in metabolic cages without food and without drink. The urine of the animals is then collected for 3 hours, whereupon their urinary bladders are once more emptied. The spontaneously excreted urine and the remaining urine obtained at the conclusion of the experiment by pressing-out the urinary bladders are collected in graduated centrifuge glasses. Sodium and potassium concentrations in the urine are determined with a flame photometer.

The following Table contains results obtained in the previously described experiment with representative compounds of formula I. In this Table there are given for each compound in question the dosage administered (in mg/kg p.o.) as well as the percentage variation in the urine volume), the sodium excretion and the potassium excretion in comparison with the control animals (i.e. in comparison with the animals treated only with aldosterone). Moreover, the Table contains data relating to the acute toxicity of the compounds investigated (LD 50 in mg/kg in the case of a single oral administration to mice).

hard gelatin capsules are lactose, maize starch or derivatives thereof, stearic acid or salts thereof etc.

Suitable excipients for soft gelatin capsules are, for example, vegetable oils, waxes, fats, semi-solid and liquid polyols etc. Depending on the nature of the active ingredient, no excipients are, however, generally necessary in the case of soft gelatin capsules.

Suitable excipients for the manufacture of solutions and syrups are, for example, water, polyols, saccharose, invert sugar, glucose and the like.

Suitable excipients for injection solutions are, for example, water, alcohols, polyols, glycerine, vegetable oils etc.

Suitable excipients for suppositories are, for example, natural or hardened oils, waxes, fats, semi-liquid or liquid polyols and the like.

The pharmaceutical preparations can, moreover, contain preserving agents, solubilising agents, stabilising agents, wetting agents, emulsifying agents, sweetening agents, colouring agents, flavouring agents, salts for varying the osmotic pressure, buffers, coating agents or antioxidants. They can also contain still other therapeutically valuable substances.

As mentioned earlier, medicaments containing one or more compounds of formula I or pharmaceutically acceptable acid additions salts thereof are also an object of the present invention, as is a process for the manufacture of such medicaments, which process comprises bringing one or more compounds of formula I or pharmaceutically acceptable acid addition salts into a galenical administration form. A further object of the present invention is, as mentioned earlier, the use of compounds of formula I and of the pharmaceutically acceptable acid addition salts thereof in the control or prevention of illnesses, especially in the control or prevention of heart failure, of hepatic ascites, of primary aldosteron-

TABLE

| $R^1$ | $R^2$ | $R^3$ | $R^4$ | Dosage mg/kg p.o. | Volume in %, based on control animals | $(Na^+)$ | $(K^+)$ | LD 50 mg/kg p.o. |
|---|---|---|---|---|---|---|---|---|
| $CH_3$ | H | F | $(CH_3)_2N-CO-$ | 1 | 152 | 330 | 160 | 2500 |
| $CH_3$ | H | F | 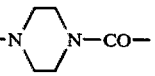 HO—CH$_2$—CH$_2$—N\_/N—CO— | 1 | 173 | 300 | 120 | >5000 |
| $CH_3$ | H | F | 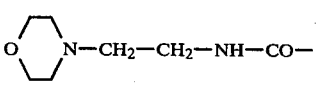 O\_/N—CH$_2$—CH$_2$—NH—CO— | 1 | 183 | 254 | 91 | 5000 |

The compounds of formula I and their pharmaceutically acceptable acid addition salts can be used as medicaments, for example in the form of pharmaceutical preparations. The pharmaceutical preparations can be administered orally, for example in the form of tablets, coated tablets, dragées, hard and soft gelatin capsules, solutions, emulsions or suspensions. The administration can, however, also be carried out by the rectal route (e.g. in the form of suppositories) or by the parenteral route (e.g. in the form of injection solutions).

For the manufacture of tablets, coated tablets, dragées and hard gelatin capsules, the compounds of formula I and their pharmaceutically acceptable acid addition salts can be processed with pharmaceutical inert, inorganic or organic excipients. Examples of such excipients which can be used for tablets, dragées and ism and of idiopathic hypertension. The dosage can vary within wide limits and is, of course, adjusted to the individual requirements in any particular case. In general, in the case of oral administration a daily dosage of about 20 mg to about 1500 mg should be appropriate.

The following Examples illustrate the present invention in more detail, but are not intended to limit its scope.

EXAMPLE 1

A stirred suspension of 5 g (0.019 mol) of 7-amino-5-phenyl-1,3-dihydro-1-methyl-2H-1,4-benzodiazepin-2-one in 70 ml of methylene chloride is treated at 0° C. with 5.83 g (0.044 mol) of N-chlorosuccinimide. Subsequently, the mixture is stirred at room temperature for 27 hours and diluted with methylene chloride. The organic phase is washed with 2 N sodium carbonate solution, dried and evaporated. The residue is chromatographed on 20 g of silica gel with methylene chloride/ethyl acetate (4:1), there being obtained 7-amino-6,8-dichloro-5-phenyl-1,3-dihydro-1-methyl-2H-1,4-benzodiazepin-2-one. After recrystallisation from methylene chloride/ethyl acetate, the product has a melting point of 228° C.

EXAMPLE 2

A solution of 50 g (0.175 mol) of 7-amino-5-(o-fluorophenyl)-1,3-dihydro-1-methyl-2H-1,4-benzodiazepin-2-one in 700 ml of methylene chloride is treated at room temperature with 27 g of N-chlorosuccinimide and the mixture is stirred for 1 hour. Subsequently, a further 27 g of N-chlorosuccinimide are added and the mixture obtained is stirred at room temperature for 17 hours. The mixture is diluted with methylene chloride, the organic phase is washed with 2 N sodium carbonate solution, dried and evaporated. After chromatography on 200 g of silica gel using methylene chloride for the elution, the residue gives 7-amino-6,8-dichloro-5-(o-fluorophenyl)-1,3-dihydro-1-methyl-2H-1,4-benzodiazepin-2-one which melts at 234° C. after recrystallisation from methylene chloride/ethyl acetate.

EXAMPLE 3

A solution of 16.7 ml of trifluoroacetic acid anhydride in 10 ml of tetrahydrofuran is added at 0° C. while stirring over a period of 5 minutes to 3.6 g (10.2 mmol) of 7-amino-6,8-dichloro-5-(o-fluorophenyl)-1,3-dihydro-1-methyl-2H-1,4-benzodiazepin-2-one and 12.2 g of sodium carbonate in 50 ml of tetrahydrofuran. After 20 minutes, the mixture is taken up in chloroform, washed with water, dried and evaporated. The residue, after recrystallisation from ether, gives N-[6,8-dichloro-5-(o-fluorophenyl)-2,3-dihydro-1-methyl-2-oxo-1H-1,4-benzodiazepin-7-yl]-2,2,2-trifluoroacetamide of melting point 238°–240° C.

EXAMPLE 4

(a) 5 g (14.25 mmol) of 7-amino-6,8-dichloro-5-(o-fluorophenyl)-1,3-dihydro-1-methyl-2H-1,4-benzodiazepin-2-one are dissolved in 325 ml of 1,2-dichloroethane under reflux. The still hot solution is subsequently added dropwise while stirring and cooling with ice to 3.73 g (37.65 mmol) of phosgene in 50 ml of ice-cold 1,2-dichloroethane, the addition being carried out in such a manner that the temperature of the mixture does not exceed 20° C. The mixture is heated under reflux for 1 hour, 80 ml of dichloroethane are allowed to distill off and 80 ml of fresh dichloroethane are added thereto. While cooling with ice, argon is conducted directly into the solution until it has reached a temperature of 10° C. There is thus obtained a 1,2-dichloroethane solution of [6,8-dichloro-5-(o-fluorophenyl)-2,3-dihydro-1-methyl-2-oxo-1H-1,4-benzodiazepin-7-yl]isocyanate.

(b) An ice-cold suspension of 6 g of sodium carbonate in 6.65 ml of dimethylamine and 40 ml of methylene chloride is added in one portion to the foregoing solution of the isocyanate, the mixture is stirred at room temperature for 24 hours, subsequently heated under reflux for 2 hours and concentrated in a rotary evaporator. The residue is taken up in 1 liter of methylene chloride/ethanol (4:1), washed with saturated sodium chloride solution, dried over magnesium sulphate and evaporated. The residue is chromatographed on 100 g of silica gel using ethyl acetate for the elution, there being obtained 3-[6,8-dichloro-5-(o-fluorophenyl)-2,3-dihydro-1-methyl-2-oxo-1H-1,4-benzodiazepin-7-yl]-1,1-dimethylurea which melts at 145°–147° C. after recrystallisation from ether.

EXAMPLE 5

A 1,2-dichloroethane solution of [6,8-dichloro-5-(o-fluorophenyl)-2,3-dihydro-1-methyl-2-oxo-1H-1,4-benzodiazepin-7-yl]isocyanate, prepared in analogy to the procedure described in paragraph (a) of Example 4 from 6 g (17.1 mmol) of 7-amino-6,8-dichloro-5-(o-fluorophenyl)-1,3-dihydro-1-methyl-2H-1,4-benzodiazepin-2-one, is treated with a suspension of 6.11 g of sodium carbonate in 6.3 ml of N-(2-hydroxyethyl)-piperazine and 40 ml of methylene chloride. The mixture is stirred at room temperature for 138 hours and concentrated in vacuo. The residue is taken up in 1.5 liter of methylene chloride/ethanol (4:1), the solution is washed with 300 ml of water, dried over magnesium sulphate and evaporated. The residue is chromatographed on 250 g of silica gel using chloroform for the elution, there being obtained N-[6,8-dichloro-5-(o-fluorophenyl)-2,3-dihydro-1-methyl-2-oxo-1H-1,4-benzodiazepin-7-yl]-4-(2-hydroxyethyl)-1-piperazinecarboxamide. After recrystallisation from methylene chloride/hexane, the product melts at 232°–233° C.

EXAMPLE 6

A 1,2-dichloroethane solution of [6,8-dichloro-5-(o-fluorophenyl)-2,3-dihydro-1-methyl-2-oxo-1H-1,4-benzodiazepin-7-yl]isocyanate, prepared in analogy to the procedure described in paragraph (a) of Example 4 from 5.5 g (15.62 mmol) of 7-amino-6,8-dichloro-5-(o-fluorophenyl)-1,3-dihydro-1-methyl-2H-1,4-benzodiazepin-2-one, is treated at room temperature all at once with a suspension of 6.11 g of sodium carbonate in 6.1 ml of N-(2-aminoethyl)morpholine and 40 ml of dichloroethane and the mixture is stirred for 114 hours. The mixture is extracted with methylene chloride/ethanol (4:1), the organic phase is washed with water, dried and evaporated. The residue is chromatographed on 250 g of silica gel using chloroform for the elution, there being obtained 1-[6,8-dichloro-5-(o-fluorophenyl)-2,3-dihydro-1-methyl-2-oxo-1H-1,4-benzodiazepin-7-yl]-3-(2-morpholinoethyl)urea. After recrystallisation from ether, the product melts at 174°–176° C.

EXAMPLE 7

A 1,2-dichloroethane solution of [6,8-dichloro-5-(o-fluorophenyl)-2,3-dihydro-1-methyl-2-oxo-1H-1,4-benzodiazepin-7-yl]isocyanate, prepared in analogy to the procedure described in paragraph (a) of Example 4 from 5 g (14.2 mmol) of 7-amino-6,8-dichloro-5-(o-fluorophenyl)-1,3-dihydro-1-methyl-2H-1,4-benzodiazepin-2-one, is treated with a suspension of 6 g of sodium carbonate in 34 ml of acetonitrile and 2 ml of methylamine. The mixture is stirred at room temperature for 66 hours, concentrated in vacuo and the residue is taken up in 1.5 liter of methylene chloride/ethanol (4:1). The organic phase is washed with saturated sodium chloride solution, dried and evaporated. The residue is chromatographed on 300 g of silica gel using methylene chloride/ethyl acetate (4:1) for the elution, there being obtained 1-[6,8-dichloro-5-(o-fluorophenyl)-2,3-dihydro-1-methyl-2-oxo-1H-1,4-benzodiazepin-7-yl]-3-methylurea. After recrystallisation from ether, the product melts at 213°–214° C.

EXAMPLE 8

(a) 40 ml (65.6 g, 0.55 mol) of thionyl chloride are added dropwise while stirring and cooling with ice to a solution of 107.2 g (0.48 mol) of carbobenzoxy-DL-alanine in 800 ml of tetrahydrofuran, the mixture is subsequently stirred at room temperature for 1 hour, a solution of 108 g (0.39 mol) of 2-amino-2'-chloro-5-nitrobenzophenone is added thereto and the resulting mixture is stirred at room temperature for 24 hours and concentrated in vacuo. The residue is treated with 600 ml of 10% sodium bicarbonate solution and extracted with methylene chloride/ethanol (9:1). The organic phase is washed with water, dried and evaporated. The residue is processed immediately.

(b) The foregoing crude product is treated with 660 ml of 33% hydrobromic acid in glacial acetic acid and the mixture is vigorously stirred at room temperature for 4 hours. The mixture is concentrated in vacuo, the residue is partitioned between 1.5 liter of water and 1.5 liter of ether, the separated aqueous phase is neutralised with 50 g of potassium carbonate and extracted with methylene chloride. The organic phase is washed with water, dried and evaporated. The residue is processed without purification.

(c) The crude product obtained according to paragraph (b), dissolved in 1 liter of toluene and 100 ml of acetic acid, is boiled at reflux for 4 hours in a water-separator and subsequently the solution is evaporated to dryness in vacuo. Residual acetic acid is removed by two-fold azeotropic evaporation with toluene. The residue, rac-5-(o-chlorophenyl)-1,3-dihydro-3-methyl-7-nitro-2H-1,4-benzodiazepin-2-one, is processed without purification.

(d) 105.7 g (0.32 mol) of crude rac-5-(o-chlorophenyl)-1,3-dihydro-3-methyl-7-nitro-2H-1,4-benzodiazepin-2-one, dissolved in 1 liter of acetone, are treated with 88.6 g (0.64 mol) of potassium carbonate and 39.9 ml (0.64 mol) of methyl iodide and the mixture is stirred at room temperature for 22 hours. The mixture is evaporated to dryness and the residue is taken up in methylene chloride. The organic phase is washed with water, dried and evaporated. Recrystallisation of the residue from methylene chloride/ethanol gives rac-5-(o-chlorophenyl)-1,3-dihydro-1,3-dimethyl-7-nitro-2H-1,4-benzodiazepin-2-one of melting point 170°–174° C.

(e) 108.9 g (0.316 mol) of rac-5-(o-chlorophenyl)-1,3-dihydro-1,3-dimethyl-7-nitro-2H-1,4-benzodiazepin-2-one are dissolved in 750 ml of concentrated hydrochloric acid. 215 g (0.95 mol) of stannous chloride are added portionwise to the solution while cooling with ice and stirring and the mixture is stirred at room temperature for 3 hours. The mixture is subsequently neutralised at 0° C. with 10 N sodium hydroxide and the aqueous phase is extracted with methylene chloride/ethanol (4:1). The organic phase is washed with water, dried and evaporated. Recrystallisation of the residue from ethyl acetate/petroleum ether yields rac-7-amino-5-(o-chlorophenyl)-1,3-dihydro-1,3-dimethyl-2H-1,4-benzodiazepin-2-one of melting point 180° C.

(f) 26.8 g (0.2 mol) of N-chlorosuccinimide are added to a solution, stirred at room temperature, of 30 g (0.095 mol) of rac-7-amino-5-(o-chlorophenyl)-1,3-dihydro-1,3-dimethyl-2H-1,4-benzodiazepin-2-one in 500 ml of methylene chloride and the mixture is stirred for 65 hours. The mixture is subsequently diluted with 400 ml of methylene chloride, 500 ml of 2 N sodium carbonate solution are added thereto, the phases are separated and the organic phase is washed with water. After drying and removal of the solvent in vacuo, the residue is chromatographed on 1 kg of silica gel using chloroform for the elution. From methylene chloride/cyclohexane there is obtained rac-7-amino-6,8-dichloro-5-(o-chlorophenyl)-1,3-dihydro-1,3-dimethyl-2H-1,4-benzodiazepin-2-one of melting point 186°–187° C.

EXAMPLE A

1-[6,8-Dichloro-5-(o-fluorophenyl)-2,3-dihydro-1-methyl-2-oxo-1H-1,4-benzodiazepin-7-yl]-3-(2-morpholinoethyl)urea can be used as follows as the active ingredient for the manufacture of pharmaceutical preparations:

| (a) Tablets | Per tablet |
|---|---|
| Active ingredient | 200 mg |
| Microcrystalline cellulose | 155 mg |
| Maize starch | 25 mg |
| Talc | 25 mg |
| Hydroxypropylmethylcellulose | 20 mg |
| | 425 mg |

The active ingredient is mixed with half of the microcrystalline cellulose and granulated with 10% solution of hydroxypropylmethylcellulose in a mixture of isopropanol and methylene chloride. The granulate is dried, sieved and mixed with the remainder of the adjuvants. The resulting mixture is pressed on a press to biplanar tablets having a diameter of 12 mm and breakbar.

| (b) Capsules | Per capsule |
|---|---|
| Active ingredient | 100.0 mg |
| Maize starch | 20.0 mg |
| Lactose | 95.0 mg |
| Talc | 4.5 mg |
| Magnesium stearate | 0.5 mg |
| | 220.0 mg |

The active ingredient is mixed with the adjuvants and sieved. After mixing again, the capsule fill mass obtained is filled into interlocking gelatin capsules of suitable size on a fully automatic capsule filling machine.

What is claimed:

1. A compound of the formula

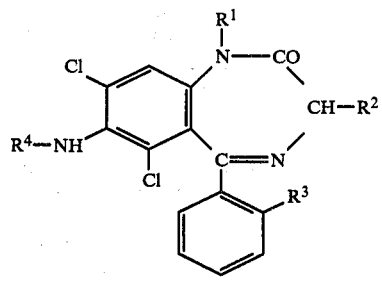

wherein $R^1$ is a lower alkyl group, $R^2$ is a hydrogen atom or a lower alkyl group, $R^3$ is a hydrogen or halogen atom, $R^4$ is a hydrogen atom or a group of the formula $R^5$-CO-, $R^6R^7$N-CO-,

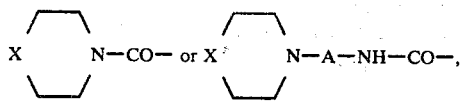

A is a lower alkylene group, X is an oxygen or sulphur atom or a group of the formula $>N-R^8$, $R^5$ is a lower alkyl or lower haloalkyl group, $R^6$ is a hydrogen atom or a lower alkyl group, $R^7$ is a lower alkyl group and $R^8$ is a hydrogen atom or a lower alkyl or lower hydroxyalkyl group, and their pharmaceutically acceptable acid addition salts.

2. The compound of claim 1, wherein $R^1$ is a methyl group.

3. The compound of claim 1 or claim 2, wherein $R^2$ is a hydrogen atom or a methyl group.

4. The compound of claims 1, 2 or 3, wherein $R^3$ is a hydrogen, fluorine or chlorine atom.

5. The compound of claims 1, 2, 3 or 4, wherein $R^4$ is a hydrogen atom or a group of the formula

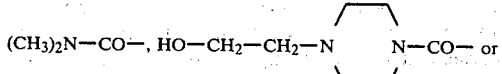

6. The compound:
3-[6,8-Dichloro-5-(o-fluorophenyl)-2,3-dihydro-1-methyl-2-oxo-1H-1,4-benzodiazepin-7-yl]-1,1-dimethylurea.

7. The compound:
N-[6,8-Dichloro-5-(o-fluorophenyl)-2,3-dihydro-1-methyl-2-oxo-1H-1,4-benzodiazepin-7-yl]-4-(2-hydroxyethyl)-1-piperazinecarboxamide.

8. The compound:
1-[6,8-Dichloro-5-(o-fluorophenyl)-2,3-dihydro-1-methyl-2-oxo-1H-1,4-benzodiazepin-7-yl]-3-(2-morpholinoethyl)urea.

9. A compound selected from the group consisting of
7-Amino-6,8-dichloro-5-phenyl-1,3-dihydro-1-methyl-2H-1,4-benzodiazepin-2-one,
7-amino-6,8-dichloro-5-(o-chlorophenyl)-1,3-dihydro-1,3-dimethyl-2H-1,4-benzodiazepin-2-one,
3-[6,8-dichloro-5-(o-fluorophenyl)-2,3-dihydro-1-methyl-2-oxo-1H-1,4-benzodiazepin-7-yl]-1-methylurea,
N-[6,8-dichloro-5-(o-fluorophenyl)-2,3-dihydro-1-methyl-2-oxo-1H-1,4-benzodiazepin-7-yl]-2,2,2-trifluoroacetamide and
7-amino-6,8-dichloro-5-(o-fluorophenyl)-1,3-dihydro-1-methyl-2H-1,4-benzodiazepin-2-one.

10. A compound of the formula

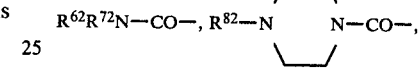

wherein $R^{41}$ is a protecting group of the group consisting of tertbutoxycarbonyl, benzoyloxycarbonyl, benzyl, tetrahydropyranyl, 2methoxy-2-propyl, methoxymethyl, β-methoxyethoxymethyl, tertbutyl and acetyl or a group of the formula

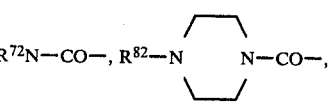

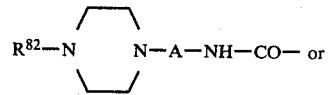

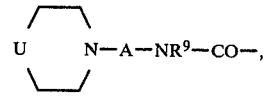

U is an oxygen or sulphur atom or a group of the formula $>N-R^{83}$, $R^{62}$ is a protecting group of the group consisting of tertbutoxycarbonyl, benzoyloxycarbonyl, benzyl, tetrahydropyranyl, 2-methoxy-2-propyl, methoxymethyl, β-methoxyethoxymethyl, tertbutyl and acetyl, $R^{72}$ is a lower alkyl group, $R^{82}$ is a protecting group of the group consisting of tertbutoxycarbonyl, benzoyloxycarbonyl, benzyl, tetrahydropyranyl, 2-methoxy-2-propyl, methoxymethyl, β-methoxyethoxymethyl, tertbutyl and acetyl or a group of the formula -A-O-V, $R^{83}$ is a hydrogen atom, a lower alkyl group, a lower hydroxyalkyl group, a protecting group of the group consisting of tertbutoxycarbonyl, benzoyloxycarbonyl, benzyl, tetrahydropyranyl, 2-methoxy-2-propyl, methoxymethyl, β-methoxyethoxymethyl, tertbutyl and acetyl or a group of the formula -A-O-V and $R^9$ and V each are a protecting group of the group consisting of tertbutoxycarbonyl, benzoyloxycarbonyl, benzyl, tetrahydropyranyl, 2-methoxy-2-propyl, methoxymethyl, β-methoxyethoxymethyl, tertbutyl and acetyl wherein $R^1$ is a lower alkyl group, $R^2$ is a hydrogen atom or a lower alkyl group, $R^3$ is a hydrogen or halogen atom and A is a lower alkylene group.

11. A compound of the formula

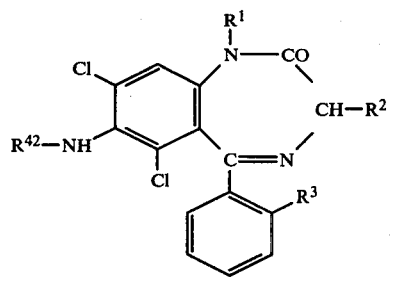

wherein $R^{42}$ is a group of the formula

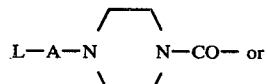 or

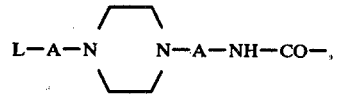

L is a leaving group selected from the group consisting of tosyloxy or alkylsulphonyloxy, $R^1$ is a lower alkyl group, $R^2$ is a hydrogen atom or a lower alkyl group, $R^3$ is a hydrogen or a halogen atom and A is a lower alkylene group.

12. A compound of the formula

XIII wherein $R^1$ is a lower alkyl group, $R^2$ is a hydrogen atom or a lower alkyl group, $R^3$ is a hydrogen or halogen atom, A is a lower alkylene group and L represents a leaving group selected from the group consisting of tosyloxy or alkylsulphonyloxy.

* * * * *